United States Patent [19]

Towsend

[11] 4,287,153

[45] Sep. 1, 1981

[54] DISPOSABLE ARTICLE WITH NON-LEACHABLE SALINE WATER INDICATOR

[76] Inventor: Marvin S. Towsend, 1365 Potomac Heights Dr., Oxon Hill, Md. 20022

[21] Appl. No.: 98,914

[22] Filed: Nov. 30, 1979

Related U.S. Application Data

[63] Continuation-in-part of Ser. No. 943,960, Sep. 20, 1978, abandoned.

[51] Int. Cl.³ .................... G01N 33/52; A61F 13/00; A61F 13/16
[52] U.S. Cl. .................................. 422/56; 128/284; 422/58
[58] Field of Search .......................... 422/56, 58, 61; 128/284

[56] References Cited

U.S. PATENT DOCUMENTS

| | | |
|---|---|---|
| 2,062,978 | 12/1936 | King . |
| 2,482,755 | 9/1949 | Ford . |
| 2,798,850 | 7/1957 | Voigtman . |
| 2,832,699 | 4/1958 | Walles . |
| 2,879,177 | 3/1959 | Nelson . |
| 2,933,460 | 4/1960 | Richter . |
| 2,937,066 | 5/1960 | Walles . |
| 2,943,000 | 6/1960 | Austin . |
| 2,965,584 | 12/1960 | Elkin . |
| 3,036,573 | 5/1962 | Voigtman . |
| 3,062,379 | 11/1962 | Bryan . |
| 3,079,350 | 2/1963 | Bernstein . |
| 3,094,494 | 6/1963 | Hopkins . |
| 3,149,000 | 9/1964 | Beicos . |
| 3,221,738 | 12/1965 | Ekberg . |
| 3,224,899 | 12/1965 | Wilson . |
| 3,311,608 | 3/1967 | Murphy . |
| 3,393,968 | 7/1968 | Segal . |
| 3,411,863 | 11/1968 | Guthrie.. |
| 3,425,545 | 2/1969 | Zemanek . |
| 3,442,687 | 5/1969 | Hagan . |
| 3,449,080 | 6/1969 | Edwards . |
| 3,463,745 | 8/1969 | Hotrichter . |
| 3,484,390 | 12/1969 | Bauman . |
| 3,544,484 | 12/1970 | Roth . |
| 3,563,243 | 2/1971 | Lindquist . |
| 3,661,860 | 5/1972 | Schwarz . |
| 3,673,110 | 6/1972 | Edwards . |
| 3,675,654 | 7/1972 | Baker . |
| 3,702,610 | 11/1972 | Sheppard ............................ 128/284 |
| 3,740,258 | 6/1973 | Walles . |
| 3,753,936 | 8/1973 | Marrs . |
| 3,816,357 | 6/1974 | Church . |
| 3,821,136 | 6/1974 | Hudgin . |
| 3,822,238 | 7/1974 | Blair . |
| 3,889,678 | 6/1975 | Chatterjee ........................... 128/284 |
| 3,900,691 | 8/1975 | Marrs . |
| 3,918,454 | 11/1975 | Korodi . |
| 3,952,746 | 4/1976 | Summers . |
| 3,997,644 | 12/1976 | Sano . |
| 4,022,211 | 5/1977 | Timmons . |
| 4,029,597 | 6/1977 | Neisius .............................. 422/56 X |
| 4,029,598 | 6/1977 | Neisius . |
| 4,108,727 | 8/1978 | Stiso .................................. 23/230 B |
| 4,163,039 | 7/1979 | Emrich ................................. 422/56 |
| 4,166,804 | 9/1979 | Blehd . |
| 4,199,550 | 4/1980 | Wielinger ......................... 422/56 X |

OTHER PUBLICATIONS

"Ion-Exchange Characteristics of Chemically Modified Cotton Fabrics," by Hoffpavir et al., *Textile Research Journal*, Sep. 1950, pp. 617-620.
*Chemical Abstracts* 60: 10878d.
*Chemical Abstracts* 61: 15337a.

*Primary Examiner*—Sidney Marantz

[57] ABSTRACT

A disposable article such as a diaper, sanitary napkin, bandage, and the like for absorbing bodily excretions; the article having a quantity of absorbent material placed between the body and a semitransparent water impermeable backsheet wherein the improvement comprises a quantity of saline water indicating material placed in close proximity to both the inner surface of the semitransparent backsheet and the excretion-absorbing material. The saline water indicating material is comprised of a water-insoluble polymeric ion exchanger and a water-insoluble polymeric exchanged-ion indicator in intimate contact with each other. The saline water indicating material may be a particulate composition or a structured material. The saline water indicating material has the three properties of, one, changing color when contacted with urine, perspiration, feces, and other saline bodily excretions; two, not having the exchanged-ion indicator or the ion exchanger leached into the urine, perspiration, feces or other saline excretions thereby not contacting the skin of the body; and, three, the changed color being observable from the outer surface of the semitransparent backsheet. The water insoluble polymeric exchanged-ion indicator component of the saline water indicating material can be a water insoluble polymeric substrate bound acid-base indicator, a water insoluble inherently polymeric acid-base indicator, a water insoluble polymeric substrate bound chelating agent, or water insoluble ion-indicating polymeric ion exchanger.

37 Claims, 2 Drawing Figures

DISPOSABLE ARTICLE WITH NON-LEACHABLE SALINE WATER INDICATOR

CROSS REFERENCE TO RELATED APPLICATION

This application is a continuation-in-part of application Ser. No. 943,960, filed Sept. 20, 1978 now abandoned.

FIELD OF THE INVENTION

The invention relates to disposable articles such as diapers, sanitary napkins, bandages, and the like, more specifically, those which indicate the presence of bodily excretions.

BACKGROUND OF THE INVENTION

A long sought after goal is to provide a disposable diaper, sanitary napkin, bandage, and the like which indicates the presence of bodily excretion while at the same time precluding subjecting the body to deleterious effects of substances present in the excretion indicating system. The following four representative prior art patents all provide for bodily excretion-indicating disposable articles using color-indicating, moisture-activated water soluble or dispersible dyes or food colorings: U.S. Pat. No. 3,675,654 of Baker et al; U.S. Pat. No. 3,918,454 of Korodi et al; U.S. Pat. No. 3,952,746 of Summers; and U.S. Pat. No. 4,022,211 of Timmons et al.

One problem associated with such prior art systems is as follows: though the water soluble or dispersible color indicating substances are disclosed as being nontoxic, it is well known that as the sciences of pharmacology and toxicology advance, numerous substances and exposure limits previously regarded as harmless or safe are thought of in a new light with respect to their toxicity. This being the case, reluctance may be felt to subject the body to any unnecessary repeated contact with water soluble or dispersible chemicals.

A second problem associated with the bodily excretion indicating systems of the prior art is their dependence upon moisture alone for their activation. Undesired activation may occur in areas of high humidity or when the disposable article may undergo inadvertent temperature and humidity cycling such as initial exposure to a high temperature-high humidity environment (such as summer storage) with subsequent exposure to a cold environment (e.g. winter storage) with consequent moisture condensation.

In view of the above deficiencies and inadequacies of the prior art in bodily excretion indicating disposable articles, it is an object of the present invention to provide a disposable article which indicates the presence of bodily excretions without employing water soluble or dispersible coloring agents.

Another object of the invention is to provide a bodily excretion indicating disposable article whose indicating system does not depend solely on the moisture component of the excretions.

Another object of the invention is to provide a disposable article for absorbing bodily excretions having a moisture absorbent saline water indicating material.

Another object of the invention is to provide a disposable article having a saline water indicating article having as a component a water insoluble polymeric acid-base indicator whose range of pH change can be outside the pH range of bodily excretions.

These and other objects are accomplished by the invention as described below.

SUMMARY OF THE INVENTION

The invention is a disposable article such as a diaper, sanitary napkin, bandage, or the like for absorbing bodily excretions having a quantity of absorbent material placed between the body and a semitransparent, water impermeable backsheet wherein the improvement comprises having a quantity of saline water indicating material placed in close proximity to both the inner surface of the backsheet and the excretion absorbing material. The saline water indicating material is comprised of a polymeric water insoluble ion exchanger and a polymeric water insoluble exchanged-ion indicator in intimate contact with each other. For purposes of indicating the presence of saline water by a color change, the water insoluble polymeric ion exchanger need have only enough ion exchange capacity and sensitivity necessary to promote a detectable color change in the water insoluble polymeric exchanged-ion indicator. Thus for purposes of the invention, the water insoluble polymeric ion exchanger may exhibit ion exchange properties considerably less than would be required in other applications of ion exchangers such as quantitative chemical analyses. The saline water indicating material may be a particulate composition or a structured material. The saline water indicating material has the three properties of, one, changing color when contacted with urine, perspiration, feces and other saline bodily excretions; two, not having the exchanged-ion indicator or the ion exchanger leached or extracted into the urine, perspiration, feces, or other saline excretions thereby not contacting the skin of the body; and, three, said color change being observable from the outer surface of the semitransparent backsheet. The polymeric water insoluble exchanged-ion indicator component of the saline water indicating material can be a polymeric substrate bound acid-base indicator, an inherently polymeric acid base indicator, a polymeric, substrate-bound chelating agent, or an ion-indicating polymeric ion exchanger.

Several different structural embodiments of the invention are contemplated. The non-leachable saline water indicating material of the disposable article of the invention may be provided in the form of: (1) a film or dusting which adheres to the inner surface of the semitransparent backsheet; (2) an amorphous stock of material which is moisture absorbent; (3) a quantity of structured absorbent material such as a sheet, foam, fabric, or film; or (4) a coating or dusting applied to either an amorphous stock of absorbent material or a structured absorbent material.

A disposable article having a quantity of saline water indicating material according to this invention may assume a variety of structure depending upon the types of and quantities of conventional absorbents and saline water indicating materials or water absorbent saline water indicating materials which are employed.

DETAILED DESCRIPTION OF THE INVENTION

Figure 1:
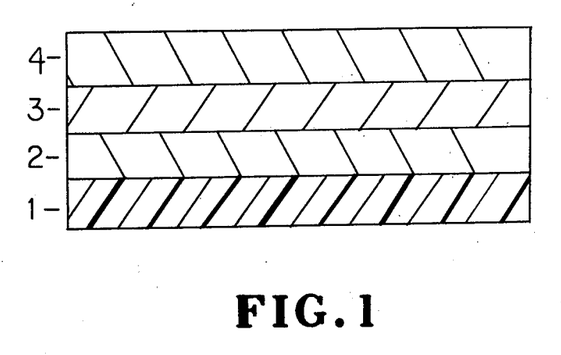
FIG. 1 shows a cross section of a disposable diaper, sanitary napkin, bandage, and the like according to the invention wherein the saline water indicating material is located between the semitransparent backsheet, and a stock of conventional absorbent material either structured or amorphous. An inner liner sheet is placed between the skin of the body and the stock of conventional absorbent.

FIG. 1 shows a generalized cross section of disposable diaper, sanitary napkin, bandage, and the like according to the invention. A prior art disposable article, for example a disposable diaper, may be comprised of a semitransparent outer water impermeable backsheet 1, a stock of conventional, non-indicating absorbent material 3, and an inner water permeable liner sheet 4. An embodiment of the invention is shown to include, in addition, a quantity of saline water indicating material 2 of the invention placed adjacent to the semitransparent backsheet 1. The saline water indicating material 2 is comprised of a water insoluble polymeric ion exchange material in intimate contact with a water insoluble polymeric exchanged-ion indicator. The saline water indicating material may be a particulate composition or a structured material. When saline water, such as present in urine, perspiration, feces, and other saline bodily excretions, contacts the saline water indicating material, the indicator material changes color thereby indicating the presence of saline water.

The saline water indicating material of the invention can assume a variety of physical forms. It can be (1) an amorphous stock material, (2) a film or dusting adhering to the inner side of the semitransparent backsheet, (3) a structured sheet, fabric, foam or film, or (4) a coating or dusting applied to either an amorphous stock of absorbent material or a structured absorbent material.

As an amorphous fibrous stock material, the saline water indicating material of the invention can be a blend of two separate polymeric fibrous materials. One such fibrous material can be a moisture absorbent polymeric substrate, such as cellulose, chemically bound with an exchanged-ion indicator to form a water insoluble polymeric, substrate-bound exchanged-ion indicator. A second such fibrous material can be a moisture absorbent polymeric substrate-bound (such as a cellulose substrate), water insoluble polymeric ion exchanger. The two fibrous materials blended together in intimate contact form a moisture absorbent, saline water indicating material of the invention.

Another moisture absorbent, saline water indicating material of the invention can be obtained by preparing a moisture absorbent cellulose bound, exchanged-ion indicator as described above, and then impregnating the cellulose-bound exchanged-ion indicator with a polymeric ion exchange resin in a manner similar to that described in U.S. Pat. No. 2,798,850 of Voigtman et al which is incorporated herein by reference. The impregnation of a polymeric absorbent cellulose substrate with a polymeric ion exchange resin results in an interpolymeric impregnation; that is, two polymers intimately impregnated. The resultant moisture absorbent cellulose substrate has a bound exchanged-ion indicator and an interpolymeric impregnated ion exchange resin in intimate contact with each other thereby forming a moisture absorbent saline water indicating material of the invention.

Figure 2:
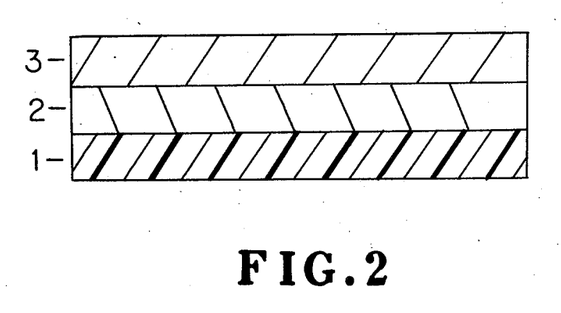
FIG. 2 shows a cross section of a disposable article according to the invention wherein the saline water indicating composition is located between the semitransparent backsheet and structured sheet, fabric, or foam of conventional absorbent material which contacts the skin of the body.

FIG. 2 shows a cross section of a three layered disposable article of the invention. The conventional absorbent 3 which contacts the skin of the body is a structured absorbent such as a fabric, sheet, or foam. The saline water indicating material 2 of the invention is adjacent to and visible from the semitransparent outer backsheet 1. As in FIG. 1, the saline water indicating material 2 shown in the embodiment of the invention of FIG. 2 can be a stock of amorphous polymeric absorbent material, an absobent sheet, an absorbent fabric, an absorbent foam, an absorbent dusting, or an absorbent film.

When the water insoluble polymeric ion exchanger is a cation exchanger in its hydrogen ion loaded form, the water insoluble polymeric exchanged-ion indicator can be an acid-base indicator in its basic form. On the other hand, when the water insoluble polymeric ion exchanger is an anion exchanger in its hydroxyl ion loaded form, the water insoluble polymeric exchanged-ion indicator can be an acid-base indicator in its acid form. The water insoluble polymeric acid-base indicator can be a polymeric substrate bound acid-base, indicator or an inherently polymeric acid-base indicator. In both cases, the mechanism of color change is as follows: ions in the aqueous bodily excretions react with the insoluble polymeric ion exchange material to cause a release of either hydrogen ions (a cation exchanger) or hydroxyl ions (an anion exchanger). The insoluble polymeric acid-base indicator, upon contacting the hydrogen ions or hydroxyl ions, then undergoes its color change. The color change of the insoluble polymeric acid-base indicator is observable from the outer side of the semitransparent backsheet. A related mode of operation involving soluble indicators used in test papers for body fluids is described in U.S. Pat. No. 3,449,080 of Edwards.

When the water insoluble polymeric ion exchanger is in the colored-chelate-forming metal cation loaded cationic form, the water insoluble polymeric exchanged-ion indicator can be a polymeric substrate bound chelating agent. In this case, the mechanism of color change is as follows: cations in the aqueous bodily excretions react with the water insoluble polymeric ion exchanger to cause a release of colored-chelate-forming metal ions. The polymeric substrate bound chelating agent, upon contacting the colored-chelate forming metal ions, then undergoes its color change.

When the water insoluble polymeric ion exchanger is in the colored-ion exchanger-forming metal anion loaded anionic form, the water insoluble polymeric exchanged-ion indicator can be a water insoluble metal anion indicating polymeric ion exchanger. In this case, two different polymeric ion exchangers are employed. For convenience of description, the first polymeric ion exchanger is the polymeric substrate bound anionic exchanger loaded with the metal anion which forms a colored product with the second ion exchanger referred to as the water insoluble exchanged-ion-indicating polymeric ion exchanger. The mechanism of color change is as follows: anions such as chloride in the aqueous bodily excretions react with the first ion exchanger to cause a release of colored-ion exchanger-forming metal anions. The second ion exchanger, the water insoluble exchanged-ion-indicating polymeric ion exchanger, forms a colored product upon contacting the metal anions released from the first ion exchanger.

The composition of the semitransparent backsheet may vary, and consequently the composition of the adhering-film or adhering-dusting of the saline water indicating material of the invention may vary accordingly. In particular, when the backsheet is comprised of an inert polyolefin as is generally the case, then an adhering indicating film composition of the invention includes a water insoluble, film-forming, dissolved or dispersed binder with a water insoluble polymeric exchanged-ion indicator and a water insoluble polymeric ion exchanger in particulate pigment form. However, the polyolefin material of the semitransparent backsheet may be pretreated in order to impart to it ion exchange characteristics. Methods for producing such ion exchange polyolefin materials are disclosed in the following U.S. patents incorporated herein by reference: U.S. Pat. Nos. 3,740,258 of Walles; 2,937,066 of Walles; 2,879,177 of Nelson et al; and 2,832,699 of Walles. In this case, the adhering, indicating water insoluble film composition includes a water insoluble film-forming, dissolved or dispersed binder with only a water insoluble polymeric exchanged-ion indicator in particulate pigment form.

In both of the preceding cases, the film adhering to the inner side of the semitransparent backsheet, of the disposable article can be obtained by blending the saline water indicating particulate pigment composition of the invention with a dissolved or dispersed water insoluble film forming binder in a liquid vehicle and then applying the blend to the inner side of the semitransparent backsheet as a coating. When the liquid vehicle evaporates, the saline water indicating particulate pigment composition is in the form of a water insoluble film, adhering to the inner side of the semitransparent backsheet. To assure optimum indicator action in the presence of saline water, the proportions of pulverized indicating composition, which is in effect a latent pigment, to the backsheet adherent binder should be such that a maximum amount of latent pigment is used with respect to a minimum amount of binder. In other words, high pigment loading is desired. Any suitable conventional method and means for applying a solid pigment/liquid vehicle as a film or coating may be used. Such techniques include brushing, spraying, roller applying, and electrostatic spraying, among others.

A saline water indicating particulate pigment composition of the invention can be applied to an inert polyolefin semitransparent backsheet by a dusting technique. An adhesive film or coating serving as a water insoluble binder can be applied to the backsheet followed by a dusting of a solid pigment form of a saline water indicating composition of the invention. The saline water indicating composition in pigment form in this case includes a solid pigment form of a water insoluble polymeric ion exchanger and a water insoluble polymeric exchanged-ion indicator. The pigment forms may be applied either in one dusting operation as a blend or applied separately in two separate dusting operations. Any suitable conventional dusting methods and means may be employed such as pneumatic spraying, sieving, and electrostatic dusting among others.

The nature of the ingredients in the saline water indicating film composition of the invention adhering to the semitransparent backsheet can vary according to the nature of the hydrophilicity of the pigmentized water insoluble polymeric exchanged-ion indicator and ion exchanger. Preferably, both the binder forming the water insoluble film and the pigmentized water insoluble polymeric exchanged-ion indicator and ion exchanger have hydrophilic characteristics. Thereby, the film or dusting adhering to the semitransparent backsheet would have an optimuum of hydrophilicity. However, it is also possible that a hydrophilic water insoluble film former may be used with a partially hydrophobic pigment. Also, a hydrophobic film former may be used with a hydrophilic pigment particularly when the binder-pigment blend is highly pigment-loaded or when pigment dusting is employed. Suitable hydrophilic water insoluble film forming compositions are disclosed in the following U.S. patents incorporated herein by reference: U.S. Pat. Nos. 3,661,860 of Schwarz; 3,821,136 of Hudgin et al; and 3,822,238 of Blair et al. Suitable hydrophilic pigmentized water insoluble polymeric exchanged-ion indicators and ion exchangers are cellulose-bound and synthetic fiber-bound acid-base indicators, chelating agents, and ion exchangers described above.

As a structured absorbent fabric, the saline water indicating material of the invention can be a fabric woven from either two separate types of fibers or one type of fiber. When woven from two types of absorbent fibers, one fiber can be a polymeric substrate bound exchanged-ion indicator, and the second fiber can be a polymeric substrate interpolymerically impregnated with a polymeric ion exchange resin or a polymeric substrate otherwise treated to have ion exchange properties. When woven from one type of absorbent fiber, the one fiber can have both bound exchanged-ion indicator and an interpolymerically impregnated ion exchange resin such as, for example, a cellulosic fibrous material having both a bound acid-base indicator and an interpolymerically impregnated hydrogen ion form of a cationic ion exchange resin.

As a structured absorbent foam, the saline water indicating material of the invention may be a well-known hydrophilic foam having a latent pigment of the invention dispersed throughout.

Several different processes are employable for obtaining a structured hydrophilic foam having saline water indicating properties. One process has the following steps: (a) a hydrophilic foam is bound by interpolymeric impregnation with an ion exchange resin to form a water insoluble bound-by-interpolymeric-impregnation polymeric ion exchanger, in a manner analogous to the process for preparing cellulose-bound-by-interpolymeric-impregnation polymeric ion exchangers disclosed in the above-mentioned U.S. Pat. No. 2,798,850 of Voigtman et al; (b) the structured foam ion exchanger product is saturated with a suspension of a pigmented water insoluble polymeric exchanged-ion indicator, such as a cellulose-substrate-bound acid-base indicator, in a liquid carrier having a hydrophilic water insoluble film former dissolved therein; (c) evaporation of the liquid carrier results in a final product wherein the structured foam has bound-by-interpolymeric-impregnation a saline water indicating material of the invention.

In a second process for obtaining a structured foam having saline water indicating properties, steps (a) and (b) in the just described process are interchanged; that is, a structured hydrophilic foam is first saturated with a suspension of a pigmented water insoluble polymeric exchanged-ion indicator in a liquid carrier having a hydrophilic water insoluble film former dissolved or dispersed therein; and, secondly, after evaporation of the liquid carrier, the foam is bound by interpolymeric impregnation with an ion exchanger as described in U.S. Pat. No. 2,798,850 of Voigtman et al.

A third process for obtaining a structured foam having saline water indicating properties comprises the steps of (a) saturating the structured foam with a suspension of both a pigmented water insoluble polymeric exchanged-ion indicator and a pigmented water insoluble polymeric-substrate-bound ion exchanger in a liquid carrier having a hydrophilic water insoluble film former dissolved therein; and (b) evaporating the solvent.

In the three above-mentioned processes for producing a structured hydrophilic foam suitable for use in a disposable article of the invention, having saline water indicating properties, the choice of liquid carrier for the hydrophilic film former and establishment of suitable liquid carrier evaporation conditions is important. The liquid carrier should be a good solvent or dispersant for the hydrophilic water insoluble film former, but a poor solvent for the structured hydrophilic foam. It should also be of relatively low boiling point. To keep to a minimum any dissolution of the structured foam, the evaporation of the liquid carrier, subsequent to saturation of the structured foam should be conducted rapidly. Use of moderate heat and strong vacuum can achieve rapid evaporation.

Structured hydrophilic foams suitable for use in conjunction with a saline water indicating material of the invention are disclosed in the following U.S. patents which are incorporated herein by reference: U.S. Pat. Nos. 2,965,584 of Elkin; 3,079,350 of Bernstein; 3,149,000 of Beicos; 3,224,899 of Wilson; 3,463,745 of Hofrichter et al; and 3,563,243 of Lindquist.

As a structured absorbent sheet, the saline water indicating material of the invention may be a sheet of cellulose-based polymeric substrate bound acid-base indicator (as disclosed in below mentioned U.S. Pat. Nos. 3,411,863 and 4,029,598) which is bound by interpolymeric impregnation with a water insoluble polymeric ion exchanger as described in above-mentioned U.S. Pat. No. 2,798,850.

As a coating applied to either a quantity of compacted amorphous stock absorbent material or a structured absorbent material, such as a sheet, fabric, or foam, the saline water indicating material of the invention can be pulverized and blended, in a liquid vehicle with a dissolved or dispersed water insoluble film forming binder and then applied to the outer-facing side of the absorbent material as a coating which is partly absorbed by capillary action below the surface of the absorbent material. When the liquid vehicle evaporates, the saline water indicating material is in the form of a water insoluble coating adhering to the absorbent material facing the inner side of the outer semitransparent backsheet.

As a dusting applied to either a quantity of compacted amorphous stock absorbent material or a structured absorbent material such as a sheet, fabric, or foam, the saline water indicating material of the invention in pigment form can be pneumatically sprayed, sieved, electrostatically sprayed or otherwise dusted onto the absorbent material which may have been pretreated with a water insoluble adhesive serving as a binder or may have been untreated.

As mentioned above, the prior art discloses, in U.S. Pat. No. 2,798,850 of Voigtman et al, the preparation of water insoluble polymeric ion exchange resins bound by interpolymeric impregnation into water insoluble, moisture absorbent cellulosic substrate materials. Therein, preparation of moisture absorbent paper bound by interpolymeric impregnation with water insoluble ion exchange resins of the cationic type, both weak and strong, and the anionic type is disclosed.

Preparation of water insoluble, moisture absorbent, polymeric substrate bound acid-base indicating material is disclosed in the prior art. In U.S. Pat. No. 4,029,598, which is incorporated herein by reference, Neisius et al disclose acid-base indicators obtained by reacting azo indicators containing both a reactive group (a group which reacts with cellulose to form a chemical bond) and at least one sulfonic acid group and/or carboxylic acid group. Among a list of cellulose-reactive groups are the preferred 2-(hydroxysulfonyloxy)-ethylsulfonyl group (abbreviated HSS) and the N-methyl-N-[2-(hydroxysulfonyloxy)-ethyl]-sulfonamido group (abbreviated N-methyl-HSS-amido).

Because of the desirability of the saline water indicator material of the invention providing an indicating color other than red because of red's similarity to the color of blood, use of a water insoluble polymeric exchanged-ion indicator undergoing color changes not in the nature of the color red is preferred. For water insoluble polymeric substrate bound acid-base indicators, Table I lists preferred cellulose fiber reactive dyestuffs, their changeover pH range, and the other-than-red color changes occurring.

TABLE I

| | Dyestuff | Change over Range | Change over Colors |
|---|---|---|---|
| (1) | 4-Anilino-3'-HSS-azobenzene-6'-carboxylic acid | 0–4.5 | deep purple-dark orange |
| (2) | 2-(2-Sulfo-4,6-dinitrophenylazo)-6-(N-methyl-HSS-amido)-1-naphthol-3-sulfonic acid | 4.0–6.5 | yellowish orange-deep green |
| (3) | 4-Anilino-3'HSS-azobenzene-6'-sulfonic acid | 0–3.0 | deep purple-yellowish orange |
| (4) | 4-(N-Methyl-HSS-anicdo)-2'-dimethylamino-azobenzene-6'-sulfonic acid | 1.0–4.0 | purple-yellow |
| (5) | 4-Methylamino-4'-(N-methyl-HSS-amido)-azobenzene-5-carboxylic acid | 0–2.0 | violet-yellow |
| (6) | 4-Methylamino-3'-methyl-4'-HSS-6'-methoxy-azobenzene-5-sulfonic acid | 0–2.5 | violet-orange |
| (7) | 4-Ethylamino-4'-(N-methyl-HSS-amido)-azobenzene-5-sulfonic acid | 0–2.0 | violet-light brown |

Additional absorbent cellulose bound acid-base indicators are disclosed in U.S. Pat. No. 3,411,863 of Guthrie et al which is incorporated herein by reference. Guthrie et al disclose bound acid-base indicators having color changes not in the red region obtained by reacting a partial 2-aminoethyl cellulose ether of cotton with an aqueous mixture of formaldehyde and an indicator having a hydrogen atom in an activated position relative to a phenolic hydroxy group such as, among others: o-cresolphthalein; 5',5''-dibromo-o-cresolsulfonphthalein; and 3',3''-dibromothymolsulfonphthalein.

As mentioned above, two aspects of the preferred saline water indicating materials of the invention are (a) that the compositions of the invention are in effect latent pigments and that (b) the produced color should be other than sanguine, the color of blood. The pigments are described as latent pigments because their saline water indicating color appears only after their exposure to saline water. The art of obtaining a spectrum of colors resulting from a blending of primary colors may be adapted to obtaining a variety of indicating colors obtained by blending a number of latent pigments of the invention. As an example, a blend of blue, green, and red pigments results in a black pigment. By blending latent blue, latent green, and latent red pigments, a black color will result when the latent black pigment is exposed to saline water. In Table II, three dyestuffs are listed. In use, these dyestuffs are individually bound to cellulose to form three individual latent pigment acid-base indicators. Dyestuff #1 will form a latent blue pigment; dyestuff #2 will form a latent green pigment; and dyestuff #3 forms a latent red pigment. A blend of the latent blue, latent green, and latent red pigments will result in a composite latent black pigment acid-base indicator. Since the latent colors of dyestuff #'s 1,2 and 3 of Table II appear on the basic side of the acid-base color change, the composite latent black pigment is used in conjunction with a water insoluble, polymeric, moisture absorbent anion exchange resin in its hydroxyl ion form. The color of the composite latent black saline water indicating material of the invention, prior to exposure to saline water is a color resulting from an intimate contact between the water insoluble polymeric moisture absorbent anionic ion exchanger and the three latent pigment acid-base indicators. Prior to exposure to saline water, this saline water indicating material is a composite yellowish-orange resulting from the color contributions as follows: anion exchanger, white; dyestuff #1 based acid-base indicator, orange-yellow; dyestuff #2 based acid-base indicator, yellow-orange; and dyestuff #3 based acid-base indicator, yellow.

After exposure to saline water, the hydroxyl ions released by the anion exchanger cause the indicating material to exhibit a composite blackish color resulting from the color contributions as follows: anion exchanger, white; dyestuff #1 based indicator, blue; dyestuff #2 based indicator, green; and dyestuff #3 based indicator, red.

TABLE II

| Dyestuff | Change over range | Change over colors |
| --- | --- | --- |
| (1) 2-(2,4-dinitrophenylazo)-6-(N-methyl-HSS-amido-1-naphthol-3-sulfonic acid | 4.0–7.5 | orangish-yellow to deep blue |
| (2) 2-(2-sulfo-4,6-dinitrophenyazo)-6-(N-methyl-HSS-amido)-1-naphthol-3-sulphonic acid | 4.0–6.5 | yellowish-orange to deep green |
| (3) 2-(2-sulfo-5-5-HSS-phenylazo)-1-naphthol-3-sulfonic acid | 9.5–12.0 | yellow to red |

In addition to the above disclosed water insoluble cellulosic substrate bound acid-base indicators suitable as latent pigments in materials of the invention, other water insoluble polymeric substrate bound acid-base indicators are suitable. Water insoluble polymeric substrate bound acid-base indicators which are bound to synthetic polymeric substrates are disclosed in U.S. Pat. No. 3,544,484 of Roth which is incorporated herein by reference. The synthetic polymeric substrate material is disclosed as containing carbonyl radicals capable of reacting with acid-base indicators. Suitable materials are disclosed as being selected from the group consisting of (a) polymers of unsaturated aldehydes having 3 to 4 carbons and (b) graft copolymers of polyvinyl alcohol and an unsaturated aldehyde having from 3 to 4 carbon atoms. Suitable acid-base indicators which react with carbonyl groups on the polymers and retain their indicator properties are in the group consisting of 4-amino-2′,3-dimethylazobenzene; p-aminoazobenzene; 2-methoxy-4-(o-methoxyphenylazo)-aniline; p-amino-α,α′azonaphthalene; benzeneazo-α-naphthylamine; and 4-(p-aminophenylazo)-benzoic acid.

The water insoluble polymeric acid-base indicators suitable as latent pigments in materials of the invention may be embodied in another form; that is, an inherently polymeric indicator, not bound to an insoluble substrate. An example of the synthesis and properties of water insoluble inherently polymeric indicators of this type are described in U.S. Pat. No. 4,166,804 of Bleha et al which is incorporated herein by reference. Bleha et al disclose inherently polymeric water insoluble acid-base indicators obtained by free radical polymerization of at least one comonomer selected from the group consisting of acrylic esters, methacrylic esters, acrylamide, methacrylamide, N-methylacrylamide, N-methylmethacrylamide, N-ethylacrylamide, N-ethylmethacrylamide, N-hydroxypropylmethacrylamide, and N-hydroxypropylmethylacrylamide with from 0.1 to 30 weight of a functional monomer selected from the group consisting of N-ethyl-N-(2-methacryloyl)aniline and N-ethyl-N-(2-methacryloylethyl)-N′-acetyl-p-phenylenediamine to form a polymer, subsequently diazo-coupling said polymer with an aromatic active agent through the available functional sites of said monomer and functionally active sites of said agent to set an acid-base indicator in said polymer.

In addition to the above disclosed water insoluble cellulosebound-by-interpolymeric-impregnation ion exchange resins suitable for use in conjunction with latent pigments in materials of the invention, other water insoluble polymeric ion exchange materials are suitable. A suitable water insoluble, moisture absorbent cellulosic substrate ion exchange material is described in "Ion-Exchange Characteristics of Chemically Modified Cotton Fabrics," by Hoffpauir et al in *Textile Research Journal,* September 1950, pp. 617–620. Other suitable cellulosic ion exchange materials are described in the previously cited U.S. Pat. No. 3,411,863 of Guthrie et al at column 4 lines 54–70 and at column 5 line 43 through column 6 line 10. Additional suitable cellulosic ion exchange materials are described in the following U.S. patents which are incorporated herein by reference: U.S. Pat. Nos. 2,482,755 of Ford et al; 3,062,379 of Bryan; 3,311,608 of Murphy; 3,393,968 of Segal; 3,425,545 of Bauman; and 3,673,110 of Edwards. These cellulosic ion exchange materials can be employed as structured absorbent materials such as fabrics, or they may be used in comminuted form as amorphous stock material.

In addition, another class of water insoluble moisture absorbent polymeric ion exchange material is described in U.S. Pat. No. 2,933,460 of Richter et al which is incorporated herein by reference. Richter et al describe a moisture absorbent synthetic polymeric fiber and fabric forming material having bound ion exchanger groups. Exemplary monomers forming suitable cation exchange synthetic polymeric fibers and fabrics are acrylic acid, methacrylic acid, itaconic acid, and maleic acid. Exemplary monomers forming suitable anion exchange polymeric fibers and fabrics are aminoalkyl acrylates, methacrylates, and itaconates. Both cation exchange and anion exchange copolymeric fibers and fabrics are also described. Synthetic polymeric films having ion exchange properties are also described.

Still another class of water insoluble moisture absorbent polymeric ion exchange material is disclosed in U.S. Pat. No. 3,094,494 of Hopkins et al which is incorporated herein by reference. Hopkins et al describe a moisture absorbent synthetic polymeric ion exchange foam obtained by polymerizing a water insoluble poly(ether-urethane) foam in the presence of a water insoluble polymeric ion exchange resin. Both anion exchange and cation exchange moisture absorbent foams are described.

Yet another class of water insoluble moisture absorbent polymeric ion exchange material is disclosed in U.S. Pat. No. 3,816,357 of Church which is incorporated herein by reference. Church discloses a cellulosic material modified by graft copolymerizing with acrylic acid or an alkacrylic acid resulting in a water insoluble, moisture absorbent synthetic polymeric material having cation ion exchange properties. U.S. Pat. No. 3,997,644 of Sano et al, incorporated herein by reference, discloses a cation ion exchange material obtained by introducing sulfonic acid groups into polyethylene fibers. Chlorosulfonic acid is used to sulfonate the polyethylene fibers.

The water impermeable semitransparent backsheet may be made of any suitable material. In embodiments of the invention described above where a water insoluble saline water indicating particulate composition of the invention is applied in pigment form as an adherent film or dusting to the inner surface of the semitransparent backsheet, a suitable water insoluble adherent binder is needed. Currently, the backsheets are generally comprised of polyolefin materials. A wide variety of adhering coating materials are known which provide an adherent water insoluble film on polyolefins and serve as a water insoluble binder for the saline water indicating composition pigments. The following U.S. patents of Hagan, Austin, Marrs, and Marrs et al, incorporated herein by reference, disclose adherent, film-forming, water insoluble binder materials for polyolefins: an ethylene-vinyl acetate copolymer as described in U.S. Pat. No. 3,442,687 of Hagan; a styrene-butadiene copolymer as described in U.S. Pat. No. 2,943,000 of Austin; a branched block copolymer of a conjugated diene and a monovinyl aromatic compound as described in U.S. Pat. No. 3,753,936 of Marrs; and a copolymer of butadiene and styrene mixed with a tackifier as described in U.S. Pat. No. 3,900,691 of Marrs et al. The polymeric binder materials disclosed above may also be used to adheringly coat amorphous stock absorbent material such as a sheet, fabric, or foam with a coating or dusting of a saline water indicating material of the invention.

Preparation of water insoluble, polymeric substrate bound chelating agents is disclosed in U.S. Pat. No. 3,484,390 of Bauman et al which is incorporated herein by reference. Bauman et al describe dithizone and oxine (8-hydroxyquinoline) chelating agents chemically bound to a cellulosic substrate. The water insoluble, polymeric substrate-bound chelating agents serve as exchanged-ion indicators. The water insoluble polymeric ion exchanger must be loaded with a cation which, upon being released, will form a colored chelate with the polymeric substrate-bound chelating agent. When the polymeric substrate bound chelating agent is oxine, then a suitable metal ion for loading the water insoluble polymeric ion exchanger is yellowish ferric ion ($Fe^{+3}$). The non-chelated oxine is also colored yellow. In operation, when sodium and other cations ions in, for example, urinereact with the ferric ion loaded polymeric ion exchanger, ferric ions are released. The ferric ions react with the polymeric substrate-bound oxine to form a green-black product.

Preparation of water insoluble polymeric substrate bound exchanged-ion-indicating ion exchange materials is disclosed in *Chemical Abstracts* 60:10878d and 61:15337a where preparation of a water insoluble diphenylcarbazide anion exchange resin is disclosed. In the hydroxyl ion loaded anionic form, the diphenylcarbazide resin is colorless. In the presence of free dichromate anions, the resin exchanges a hydroxyl ion for a dichromate ion and turns to a red-violet coloration. For a saline water indicating material of the invention, the water insoluble polymeric ion exchange resin can be an anion exchange resin in the dichromate ion loaded form comminuted into a powdered form. The water insoluble polymeric exchanged-ion indicator can be a water insoluble diphenylcarbazide resin in a granular form. The two particulate materials blended together form a saline water indicating material. In operation, when chloride and other anions in, for example, urine react with the dichromate loaded anion exchanger, dichromate ions are released. The dichromate ions react with the substrate-bound diphenylcarbazide resin to form a red-violet product.

It has been suggested in the prior art of disposable diapers, in particular, as described in U.S. Pat. No. 4,022,211 of Timmons et al cited above, that for indicating exposure to urine, a color change resulting in a disappearing colored pattern is preferred over a color change resulting in the appearance of a color. This mode of operation is easily obtained with the instant invention by employing a saline water indicating material of the invention having a latent pigment showing a darkly colored form prior to exposure to saline water and showing a lightly colored form as it indicates the presence of the exchanged ions after exposure to urine. For example, in a saline water indicating material comprising a blend of a hydrogen ion loaded water insoluble polymeric cationic ion exchanger and a water insoluble polymeric substrate bound acid-base indicator, prior to exposure to saline water the polymeric substrate bound acid-base indicator can be in the basic form as a darkly colored pigment. Upon exposure to hydrogen ions, released by the ion exchanger having contacted sodium ions in urine, the substrate bound acid-base indicator would convert to a lightly colored acid form. Flexographic printing is particularly useful for applying patterns. Patterns may also be obtained by using masks with spraying. Any other suitable conventional coating or dusting pattern-forming process may be used for applying a pigmented saline water indicating material of the invention to either the water impermeable semitransparent backsheet or the conventional absorbent material.

The ratio of the water insoluble polymeric ion exchanger to water insoluble polymeric exchanged-ion indicator should be adjusted so that the exchanged-ion indicator is in excess of chemical equivalents with respect to the ion exchanger. This excess in chemical equivalents of exchanged-ion indicator with respect to ion exchanger helps prevent the free, exchanged-ions from contacting the skin of the body of the wearer of the disposable article. For example, for indicating the presence of urine using a saline water indicating material of the invention which is comprised of a hydrogen ion loaded water insoluble polymeric cation ion exchanger in intimate admixture with a cellulose bound water insoluble acid-base indicator in its basic form, the released free hydrogen ions resulting from the sodium ion exchange (in the environment of urine) would react immediately with the acid-base indicator and would be prevented from contacting the skin of the body.

By using a saline water indicating material comprised of a water insoluble polymeric cation exchanger in its hydrogen ion loaded form in intimate admixture with a water insoluble polymeric acid-base indicator in its basic form, acid-base indicators whose pH change range is outside the pH range of bodily exretions can be used. Because of the intimate nature of the admixture of the two components, when free hydrogen ions are released from the ion exchanger, they are in relatively high concentration with respect to the intimately admixed acid-base indicator. This relatively high concentration of acidity in immediate proximity to and in immediate contact with the acid-base indicator permits utilization of acid-base indicators whose color change pH range is outside the pH range of the saline bodily exretions whose presence is indicated.

The amount of water insoluble polymeric ion exchanger needed to be present is relatively small because of the extreme sensitivity of most water insoluble polymeric acid-base indicators in the presence of small amounts of free hydrogen ions and other exchanged-ion indicators in the presence of other exchanged ions.

Thus, by using only a small amount of water insoluble polymeric ion exchanger in the presence of an excess of chemical equivalents of a water insoluble polymeric acid-base indicator, a broad range of sensitive acid-base indicators can be used without subjecting the body of the wearer of the disposable article to harmful amounts of added free acidity in addition to that already present in the saline water bodily excretions.

In the use of the saline water indicating material of the invention in a disposable article, another factor which allows for the use of small amounts of ion exchanger in the presence of sensitive acid-base indicators and which precludes harmful release of free hydrogen ions which would contact the skin of the body of the wearer is the lack of a highly mobile liquid phase in the article. The moisture absorbent materials soak up the saline water and to large extent, immobilize the liquid phase. Thus, dilution of the free hydrogen ions released by the ion exchanger in the presence of the acid-base indicator is impeded. The greater the absorbency power of the absorbents in the disposable article, the greater the efficiency of the saline water indicating material in indicating the presence of saline water.

The above description, it is believed, has described and disclosed the present invention in such a complete fashion as to enable any one with ordinary skill in the art to utilize the present invention to its fullest extent. The following preferred specific embodiments, presented below as examples, are to be construed as merely illustrative and not intended to limit the scope of the invention which is defined in the claims.

EXAMPLE I

When a disposable article having a quantity of absorbent material for absorbing bodily excretions is fabricated as shown in FIG. 1 or 2 herein, a quantity of saline water indicating material 2 is placed between the absorbent material 3 and a semitransparent, water impermeable polyolefin backsheet 1. The color change of the saline water indicating material is observable from the outward side of the semitransparent backsheet.

Conventional absorbent disposable articles and their methods of manufacture are described in the following U.S. patents incorporated herein by reference: U.S. Pat. Nos. 2,062,978 of King; 3,036,573 of Voigtman et al; 3,221,738 of Ekberg et al; 3,675,654 of Baker et al; and 4,022,211 of Timmons et al.

The saline water indicating material can be comprised of a sheet of a cellulose-bound water insoluble acid-base indicator in its basic form bound by interpolymeric impregnation with a hydrogen ion loaded cationic phthalein-aldehyde water insoluble ion exchange resin as described in U.S. Pat. No. 2,798,850 at column 3, lines 35–75 incorporated herein by reference.

The cellulose-bound, water insoluble acid-base indicator can be obtained by reacting cellulose with the reactive dyestuff 2-(2-sulfo-4,6-dinitrophenylazo)-6-(N-methyl-N-[2-(hydroxysulfonyloxy)-ethyl]-sulfonamido)-1-naphthol-3-sulfonic acid as described U.S. Pat. No. 4,029,598 Example 1c, incorporated herein by reference, by substituting dyestuff #47 for dyestuff #1. The bound acid-base indicator is washed neutral with deionized water and dried before used in the disposable article. Before exposure to saline water, such as urine, the disposable article exhibits a green color (the basic form) when viewed from the outward side of the semitransparent backsheet. After exposure to saline water, a color change occurs and a yellowish-orange color is visible; this is the acid form resulting from contact with the hydrogen ions released by the hydrogen ion loaded ion exchange resin upon exposure to such cations in the urine as sodium and potassium.

EXAMPLE II

A disposable article can be fabricated having the same general structure as shown in FIG. 1 or 2 except that the saline water indicating material 2 is comprised of a fabric of a cellulose-bound, water insoluble acid-base indicator bound by interpolymeric impregnation with a water insoluble phthalein-aldehyde hydrogen ion loaded cationic exchange resin as described in Example I. The fabric of cellulose bound, water insoluble acid-base indicator is obtained by reacting a partial 2-aminoethyl cellulose ether of cotton in fabric form with an aqueous mixture of formaldehyde and an acid-base indicator having a hydrogen in an activated position relative to a phenolic hydroxy group such as 5',5''-dibromo-o-cresolsulfonphthalein in the manner as described in U.S. Pat. No. 3,411,863 at column 9 lines 35–45 incorporated herein by reference.

Before exposure to saline water, the disposable article exhibits a greenish-black color (the basic form) when viewed from the outward side of the semitransparent backsheet. After exposure to saline water, a color change occurs and a yellow color is visible; this is the acid form resulting from contact with the hydrogen ions released by the hydrogen ion loaded ion exchange resin upon exposure to the saline cations. Thus a darkly colored pattern can be transformed into a lightly colored pattern upon exposure to saline water.

EXAMPLE III

A disposable article can be fabricated having the same general structure as shown in FIG. 1 or 2 except that the saline water indicating material 2 is in the form of particles held by a coating matrix. The particles can be a blend of water insoluble polymeric ion exchanger particles with inherently polymeric water insoluble hydrophilic polyurethane film. The coating can be applied as pigment suspended in a dissolved vehicle; or the vehicle may be applied first, then followed by a dusting of the vehicle while still tacky.

In particular, a pigmentized, cellulose-bound-by-interpolymeric-impregnation, water insoluble cationic ion exchanger as described in U.S. Pat. No. 2,798,850 at column 3, lines 35-75 can be blended with a pigmentized inherently polymeric water insoluble acid-base indicator as described in U.S. Pat. No. 4,166,804 at column 3 lines 15-20, incorporated herein by reference, to form a pigmentized saline water indicating material. The pigmentized material blend can be dispersed in a vehicle comprised of a solution of a hydrophilic polyurethane film dissolved in the solvent tetrahydrofuran as described in U.S. Pat. No. 3,661,860 column 2, lines 52-68, incorporated herein by reference. The pigment-vehicle dispersion may be brushed, sprayed, or otherwise applied to either the inner side of the semitransparent backsheet or the outward facing side of the adsorbent. As the solvent evaporates, an adherent saline water indicating coating is formed.

Alternately, the film former solution may be applied alone, followed by a dusting of the particulate saline water indicating material blend onto the film while still tacky, before it dries completely. After drying, an adherent saline water indicating dusting results.

EXAMPLE IV

A disposable article can be fabricated having the same general structure as shown in FIGS. 1 or 2 except for the constitution of the saline water indicating material 2. A water insoluble cellulose-bound-by-interpolymeric-impregnation anionic ion exchanger, such as a modified-amine ion exchanger, is prepared as described in U.S. Pat. No. 2,798,850 at column 7 lines 55-75 incorporated herein by reference. The ion exchanger is comminuted and treated to be in its hydroxyl ion loaded anionic form. The water insoluble polymeric acid-base indicator is a water insoluble, synthetic polymeric substrate-bound acid-base indicator as described in U.S. Pat. No. 3,544,484 at column 3 line 74 through column 4 line 6, incorporated herein by reference. When the two particulate materials are blended, a pigmentized saline water indicating material is obtained. By techniques described in Example III, a saline water indicating material in the form of a coating or dusting can be obtained.

EXAMPLE V

A disposable article can be fabricated having the same general structure as shown in FIGS. 1 or 2 except for the constitution of the saline water indicating material 2. A water insoluble hydrophilic polyurethane foam sheet can be impregnated with a coating of vehicle-pigment dispersion as described above in Example III. When the tetrahydrofuran solvent evaporates, the hydrophilic foam sheet is bound by interpolymeric impregnation with a water insoluble saline water indicating hydrophilic polymeric coating. The steps of impregnation of the hydrophilic foam sheet and evaporation of the tetrahydrofuran solvent-dispersant should be done rapidly to minimize dissolution of the hydrophilic foam sheet by the tetrahydrofuran.

EXAMPLE VI

A disposable article can be fabricated having the same general structure as shown in FIGS. 1 or 2 except for the constitution of the saline water indicating material 2. A water insoluble, modified-cellulose cation ion exchanger is prepared from comminuted cotton by the method described in U.S. Pat. No. 3,424,545, incorporated herein by reference, at column 4 line 72 through column 5 line 8. The cation exchanger is then loaded with ferric ions by treating with an aqueous solution of ferric chloride. The ferric ion loaded cation exchanger is rinsed thoroughly with deionized water to remove unbound ferric ions and dried. The result is a pigmentized, ferric ion loaded water insoluble cation ion exchanger.

A water insoluble pigmentized cellulose bound 8-hydroxyquinoline (oxine) is prepared as described in U.S. Pat. No. 3,484,390, incorporated herein by reference, at column 3 lines 47 through 53 and lines 12 through 45.

By blending the pigmentized water insoluble ferric ion loaded cellulosic cation exchanger with the pigmentized water insoluble cellulose-bound 8-hydroxyquinoline (oxine) chelating agent, a pigmentized saline water indicating material is obtained. The pigmentized blend may be used as a film coating or dusting as described in Example III.

When saline water, such as urine, contacts the ferric ion loaded cation exchanger, sodium and other cations in the urine exchange, with the ferric ion thereby releasing free ferric ions. The free ferric ions react with the cellulose-bound 8-hydroxyquinoline to form a greenish-black color. Thus the presence of saline water is indicated by the color change from light yellow (the color of unchelated ferric ion) to greenish-black (the color of the ferric ion-oxine chelate).

EXAMPLE VII

A disposable article can be fabricated having the same general structure as shown in FIGS. 1 or 2 except for the constitution of the saline water indicating material 2. A water insoluble polymeric anion exchanger is prepared as described in U.S. Pat. No. 2,798,850 at column 7 lines 55 through 75. The ion exchanger is comminuted and treated by an aqueous solution of sodium dichromate to convert the anion exchanger into its dichromate anion loaded form. The dichromate loaded anion exchanger is rinsed thoroughly with deionized water to remove any free dichromate ions. The dichromate loaded anion exchanger is then dried and ready for subsequent use. It is colored orange.

A water insoluble polymeric dichromate-ion-indicating anion exchanger is a pigmentized diphenylcarbazide anion exchanger which is prepared as follows: dissolve 8.4 g. melamine in 50 ml. of 37% formaldehyde solution; heat; add 3 g. of urea dissolved in 10 ml. water; add 4.8 g. sym-diphenylcarbazide in 50 ml. lf acetic acid and stir thoroughly; heat at 80° C. under reflux for 3 hrs.; and leave 24 hrs. at room temperature. The resulting white hard gel resin is ground and sieved through a nest of sieves such as U.S. Standard Sieves #'s 50 and 60. The powder passing through the #50 sieve and retained on the #60 sieve is washed with $H_2O$, 1 N $H_2SO_4$, $H_2O$, 1 N $NH_4OH$, $H_2O$, and 1 N $H_2SO_4$. The resin is then treated with 0.001 M $K_2CR_2O_7$ in 0.2 N $H_2SO_4$; left for 24 hrs.; washed with 2 N $H_2SO_4$; reduced with 0.1 M $Na_2S_2O_4$ in 0.1 N $Na_2CO_3$; washed with $H_2O$, 1 N $H_2SO_4$, and $H_2O$; and allowed to dry four days at room temperature. The resin is in a pigmentized white granular form.

The two pigments are then blended; that is, the pigmentized dichromate loaded anion exchanger is blended with the pigmentized diphenylcarbazide anion exchanger to form a pigmentized water insoluble polymeric saline water indicating material. This material is colored light orange and is suitable for use in coatings or dusting as described in Example III. When chloride and other anions in saline water, such as urine, contact the dichromate loaded anion exchanger, dichromate ions are released. The free dichromate ions react with the diphenylcarbazide resin to form a red-violet color. Thus, saline water is indicated by a color change from light orange to red violet.

EXAMPLE VIII

A disposable article can be fabricated having the same general structure as shown in FIGS. 1 or 2 except for the constitution of the saline water indicating material 2. A plurality of sheets of cellulose bound, water insoluble acid-base indicator, bound by interpolymeric impregnation with a water insoluble polymeric cation ion exchanger, can be prepared as described in Example I. The sheets of the thusly prepared saline water indicating material can be shredded and chopped to form an amorphous stock of a moisture absorbent saline water indicating material having the properties of both being highly water absorbent and indicating the presence of saline water by a color change.

It is to be understood that changes and variations can be made without departing from the scope of the invention which is defined in the claims.

What is claimed is:

1. A disposable article for absorbing bodily excretions, comprising:
   a quantity of absorbent material for absorbing the bodily excretions;
   a semitransparent water impermeable backsheet for retaining said absorbent material and the absorbed excretions; and
   a quantity of non-leachable saline water indicating material placed in contact with said absorbent material and in close proximity to said semitransparent backsheet for indicating the presence of the absorbed excretions.

2. A disposable article for absorbing bodily excretions, comprising:
   a quantity of absorbent material for absorbing the bodily excretions;
   a semitransparent water impermeable backsheet for retaining said absorbent material and the absorbed excretions; and
   a quantity of non-leachable saline water indicating material placed in contact with said absorbent material and in close proximity to said semitransparent backsheet;
   said saline water indicating material comprising, in intimate contact, a water insoluble polymeric ion exchanger and a water insoluble polymeric exchanged-ion indicator for indicating the presence of the absorbed excretions.

3. A disposable article as described in claim 2, wherein:
   (a) said water insoluble polymeric ion exchanger is a hydrogen ion loaded cation exchanger; and
   (b) said water insoluble polymeric exchanged-ion indicator is an acid-base indicator in its basic form.

4. A disposable article as described in claim 3 wherein said water insoluble polymeric acid-base indicator is a cellulose bound acid-base indicator obtained by reacting cellulose with a reactive dyestuff from the group consisting of:
4-anilino-3'-(2-hydroxysulfonyloxy-ethylsulfonyl)-azobenzene-6'-carboxylic acid;
2-(2-sulfo-4,6-dinitrophenylazo)-6-(N-methyl-N-[2-(hydroxysulfonyloxy)-ethyl]-sulfonamido)-1-naphthol-3-sulfonic acid;
4-anilino-3'-(2-hydroxysulfonyloxy-ethylsulfonyl)-azobenzene-6'-sulfonic acid;
4-(N-methyl-N-[2-(hydroxysulfonyloxy)-ethyl]-sulfonamido)-2'-dimethylaminoazobenzene-6'-sulfonic acid;
4-methylamino-4'-(N-methyl-N-[2-(hydroxysulfonyloxy)-ethyl]-sulfonamido)-azobenzene-5-carboxylic acid;
4-methylamino-3'-methyl-4'-(2-hydroxysulfonyloxy-ethylsulfonyl)-6'-methoxy-azobenzene-5-sulfonic acid;
2-[2-sulfo-5-(2-hydroxysulfonyloxy-ethylsulfonyl)-phenylazo]-1-naphthol-3-sulfonic acid;
2-(2,4-dinitrophenylazo)-6-(N-methyl-N-[2-(hydroxysulfonyloxy)-ethyl]-sulfonamido)-1-naphthol-3-sulfonic acid; and mixtures thereof.

5. A disposable article as described in claim 3 wherein said water insoluble polymeric acid-base indicator is obtained by reacting a partial 2-aminoethyl cellulose ether of cotton with an aqueous mixture of formaldehyde and an acid-base indicator having a hydrogen atom in an activated position relative to a phenolic hydroxy group such as acid-base indicators in the group consisting of o-cresolphthalein; 5',5''-dibromo-o-cresolsulfonphthalein; and 3',3''-dibromothymolsulfonphthalein.

6. A disposable article as described in claim 3 wherein said water insoluble polymeric acid-base indicator is an acid-base indicator bound to a synthetic polymeric substrate.

7. A disposable article as described in claim 3 wherein said water insoluble polymeric acid-base indicator is an inherently polymeric acid-base indicator.

8. A disposable article as described in claim 2, wherein:
   (a) said water insoluble polymeric ion exchanger is a hydroxyl ion loaded anion exchanger; and
   (b) said water insoluble polymeric exchanged-ion indicator is an acid-base indicator in its acid form.

9. A disposable article as described in claim 8 wherein said water insoluble polymeric acid-base indicator is a cellulose bound acid-base indicator obtained by reacting cellulose with a reactive dyestuff from the group consisting of:
4-anilino-3'-(2-hydroxysulfonyloxy-ethylsulfonyl)-azobenzene-6'-carboxylic acid;
2-(2-sulfo-4,6-dinitrophenylazo)-6-(N-methyl-N-[2-hydroxysulfonyloxy)-ethyl]-sulfonamido)-1-naphthol-3-sulfonic acid;
4-anilino-3'-(2-hydroxysulfonyloxy-ethylsulfonyl)-azobenzene-6'-sulfonic acid;
4-(N-methyl-N-[hydroxysulfonyloxy)-ethyl]-sulfonamido)-2'-dimethylaminoazobenzene-6'-sulfonic acid;
4-methylamino-4'-(N-methyl-N-[2-(hydroxysulfonyloxy)-ethyl]-sulfonamido)-azobenzene-5-carboxylic acid;
4-methylamino-3'-methyl-4'-(2-hydroxysulfonyloxy-ethylsulfonyl)-6'-methoxy-azobenzene-5-sulfonic acid;
2-[2-sulfo-5-(2-hydroxysulfonyloxy-ethylsulfonyl)-phenylazo]-1-naphthol-3-sulfonic acid;
2-(2,4-dinitrophenylazo)-6-(N-methyl-N-[2-(hydroxysulfonyloxy)-ethyl]-sulfonamido)-1-naphthol-3-sulfonic acid; and mixtures thereof.

10. A disposable article as decribed in claim 8 wherein said water insoluble polymeric acid-base indicator is obtained by reacting a partial 2-aminoethyl cellulose ether of cotton with an aqueous mixture of formaldehyde and an acid-base indicator having a atom in an activated position relative to a phenolic hydroxy group such as acid-base indicators in the group consisting of o-cresolphthalein; 5',5''-dibromo-o-cresolsulfonphthalein; and 3',3''-dibromothymolsulfonphthalein.

11. A disposable article as described in claim 8 wherein said water insoluble polymeric acid-base indicator is an acid-base indicator bound to a synthetic polymeric substrate.

12. A disposable article as described in claim 8 wherein said water insoluble polymeric acid-base indicator is an inherently polymeric acid-base indicator.

13. A disposable article as described in claim 2, wherein:
(a) said water insoluble polymeric ion exchanger is a cation exchanger in a colored-chelate-forming metal cation loaded form; and
(b) said water insoluble polymeric exchanged-ion indicator is a substrate bound chelating agent.

14. A disposable article as described in claim 13, wherein:
(a) said colored-chelate-forming metal cation loaded ion exchanger is a ferric ion loaded cationic exchanger; and
(b) said substrate bound chelating agent is cellulose substrate bound 8-hydroxyquinoline.

15. A disposable article as described in claim 2, wherein:
(a) said water insoluble polymeric ion exchanger is an anion exchanger in a colored-ion exchanger-forming anion form; and
(b) said water insoluble polymeric exchanged-ion indicator is an exchanged-ion-indicating anionic exchanger.

16. A disposable article as described in claim 15, wherein
(a) said anion exchanger in a colored-ion exchanger-forming anion form is an anion exchanger in the dichromate anion loaded form; and
(b) said exchanged-ion-indicating anionic ion exchanger is a diphenylcarbazide ion exchange resin.

17. A disposable article as described in claim 2 wherein said water insoluble polymeric ion exchanger is a cellulose substrate bound ion exchanger.

18. A disposable article as described in claim 2 wherein said water insoluble polymeric ion exchanger is a synthetic polymeric ion exchanger.

19. A disposable article as described in claim 18 wherein said synthetic polymeric ion exchanger is a polyolefin ion exchanger.

20. A disposable article as described in claim 18 wherein said synthetic polymeric ion exchanger is formed from monomers selected from the group consisting of acrylic acid, methacrylic acid, itaconic acid, maleic acid, aminoalkylacrylates, methacrylates, and itaconates.

21. A disposable article as described in claim 2 wherein said water insoluble polymeric exchanged-ion indicator is a cellulose substrate bound exchanged-ion indicator.

22. A disposable article as described in claim 21 wherein said cellulose substrate bound exchanged-ion indicator is a cellulose substrate bound acid-base indicator.

23. A disposable article as described in claim 21 wherein said cellulose substrate bound exchanged-ion indicator is a cellulose substrate bound chelating agent.

24. A disposable article as described in claim 23 wherein said cellulose substrate bound chelating agent is cellulose substrate bound 8-hydroxyquinoline.

25. A disposable article as described in claim 2 wherein said saline water indicating material is in the form of an amorphous stock of absorbent material.

26. A disposable article as described in claim 2 wherein said saline water indicating material as in the form of a dusting of particulate material.

27. A disposable article as described in claim 26 wherein said dusting of particulate material is applied to the semitransparent backsheet.

28. A disposable article as described in claim 26 wherein said dusting of particulate material is applied to the quantity of absorbent material facing the semitransparent backsheet.

29. A disposable article as described in claim 2 wherein said saline water indicating material is in the form of a coating.

30. A disposable article as described in claim 29 wherein said coating is applied to the semitransparent backsheet.

31. A disposable article as described in claim 29 wherein said coating is applied to the quantity of absorbent material facing the semitransparent backsheet.

32. A disposable article as described in claim 29 wherein said coating is comprised of a pigmentized saline water indicating material in a hydrophilic film.

33. A disposable article as described in claim 2 wherein said saline water indicating material is in the form of a structured absorbent material.

34. A disposable article as described in claim 33 wherein said structured absorbent material is in the form of a fabric.

35. A disposable article as described in claim 33 wherein said structured absorbent material is in the form of a sheet.

36. A disposable article as described in claim 33 wherein said structured absorbent material is in the form of a foam.

37. A disposable article as described in claim 2 wherein said water insoluble polymeric ion exchanger and said water insoluble polymeric exchanged-ion indicator are in intimate contact as a result of interpolymeric impregnation.

* * * * *